United States Patent [19]
Maynard

[11] Patent Number: 6,133,547
[45] Date of Patent: Oct. 17, 2000

[54] DISTRIBUTED ACTIVATOR FOR A TWO-DIMENSIONAL SHAPE MEMORY ALLOY

[75] Inventor: Ronald S. Maynard, Sunnyvale, Calif.

[73] Assignee: Medtronic, Inc., Minneapolis, Minn.

[21] Appl. No.: 08/708,586

[22] Filed: Sep. 5, 1996

[51] Int. Cl.[7] ............................................. H05B 1/00
[52] U.S. Cl. ...................... 219/209; 219/528; 604/281; 337/140
[58] Field of Search ........................ 219/209, 200, 219/201, 528, 549, 508; 604/281; 337/140

[56] References Cited

U.S. PATENT DOCUMENTS

| | | | |
|---|---|---|---|
| 3,598,125 | 8/1971 | Cogley | 128/346 |
| 4,164,045 | 8/1979 | Bokros et al. | 3/1.4 |
| 4,337,090 | 6/1982 | Harrison | 148/402 |
| 4,490,975 | 1/1985 | Yaeger et al. | 60/527 |
| 4,524,343 | 6/1985 | Yaeger et al. | 60/527 |
| 4,533,411 | 8/1985 | Melton | 148/402 |
| 4,543,090 | 9/1985 | McCoy | 604/95 |
| 4,553,393 | 11/1985 | Rouff | 337/140 |
| 4,559,512 | 12/1985 | Yaeger et al. . | |
| 4,565,589 | 1/1986 | Harrison | 148/402 |
| 4,601,705 | 7/1986 | McCoy | 604/95 |
| 4,631,094 | 12/1986 | Simpson et al. | 148/11.5 |
| 4,665,906 | 5/1987 | Jervis | 128/92 |
| 4,700,541 | 10/1987 | Gabriel et al. | 337/140 |
| 4,753,223 | 6/1988 | Bremer | 604/281 |
| 4,758,222 | 7/1988 | McCoy | 604/95 |
| 4,770,725 | 9/1988 | Simpson et al. | 148/402 |
| 4,776,541 | 10/1988 | Maynard | 244/165 |
| 4,777,799 | 10/1988 | McCoy et al. | 60/528 |
| 4,790,624 | 12/1988 | Van Hoye et al. | 385/118 |
| 4,884,557 | 12/1989 | Takehana et al. | 604/281 |
| 4,918,919 | 4/1990 | McCoy et al. | 60/528 |
| 4,990,883 | 2/1991 | Escobar et al. . | |
| 4,994,727 | 2/1991 | McCoy | 604/95 |
| 5,055,101 | 10/1991 | McCoy | 604/95 |
| 5,061,914 | 10/1991 | Busch et al. | 337/140 |

(List continued on next page.)

FOREIGN PATENT DOCUMENTS

| | | |
|---|---|---|
| 0 326 426 A2 | 2/1989 | European Pat. Off. ........ B29C 61/00 |
| 0 558 352 A1 | 1/1993 | European Pat. Off. ........ A61B 17/11 |
| 0 554 128 | 12/1993 | European Pat. Off. .......... F03G 7/06 |
| 61-185082 | 8/1986 | Japan . |
| 61-190177 | 8/1986 | Japan . |
| 3-5128 | 1/1991 | Japan . |
| 7-75355 | 3/1995 | Japan . |
| 7-247954 | 9/1995 | Japan . |
| 1696298 | 12/1991 | U.S.S.R. . |
| WO 92/15582 | 12/1990 | WIPO ............................... A61F 2/06 |
| WO 92/01425 | 2/1992 | WIPO ............................... A61F 2/06 |
| WO 94/19051 | 9/1994 | WIPO ........................... A61M 37/00 |
| 9534189 | 12/1995 | WIPO . |

OTHER PUBLICATIONS

Busch, J.D., et al., "Prototype Micro–Valve Actuator".
Ikuta, K., et al., Crystallographic Analysis of Tni Shape Memory Alloy Thin Film for Micro Actuator.
Kuribayashi, K., "Reversible SMA Actuator for Micron Sized Robot".

Primary Examiner—Teresa Walberg
Assistant Examiner—Shawntina Fuqua
Attorney, Agent, or Firm—Reed A. Duthler; Harold R. Patton

[57] ABSTRACT

A distributed activation system for a unitary sheet of electrically conductive or insulative shape memory alloy having a sufficiently small section to limit the lateral flow of heat including at least one heating element disposed on the shape memory alloy sheet for locally heating an adjacent portion of the sheet such that the adjacent portion assumes a predetermined shape when activated to its threshold temperature. The activation system may be configured for shape memory alloy apparatus and related methods in combination with a control system for selectively activating discrete shape memory alloy portions with various combinations of at least one heating element that receive an adjustable current such that the resultant local heating causes the sheet to assume a desired overall shape. Methods of forming and selectively activating two-dimensional sheets of electrically conducive and insulative shape memory alloy are further provided.

32 Claims, 7 Drawing Sheets

U.S. PATENT DOCUMENTS

| | | | |
|---|---|---|---|
| 5,067,957 | 11/1991 | Jervis | 606/108 |
| 5,078,684 | 1/1992 | Yasuda | 604/95 |
| 5,090,956 | 2/1992 | McCoy | 604/95 |
| 5,114,402 | 5/1992 | McCoy | 604/95 |
| 5,135,517 | 8/1992 | McCoy | 604/281 |
| 5,165,897 | 11/1992 | Johnson | 434/113 |
| 5,176,544 | 1/1993 | Abujudom, II et al. | 439/878 |
| 5,188,111 | 2/1993 | Yates et al. | 128/657 |
| 5,190,546 | 3/1993 | Jervis | 606/78 |
| 5,229,211 | 7/1993 | Murayama et al. | 428/424.4 |
| 5,254,130 | 10/1993 | Poncet et al. | 606/206 |
| 5,279,559 | 1/1994 | Barr | 604/95 |
| 5,309,717 | 5/1994 | Minch | 60/527 |
| 5,334,168 | 8/1994 | Hemmer | 604/281 |
| 5,335,498 | 8/1994 | Komatsu et al. | 60/528 |
| 5,345,937 | 9/1994 | Middleman et al. | 128/657 |
| 5,405,337 | 4/1995 | Maynard | 602/128 |
| 5,481,184 | 1/1996 | Jacobsen | 324/106 |
| 5,482,029 | 1/1996 | Sekiguchi et al. | 604/281 |
| 5,531,685 | 7/1996 | Hemmer et al. | 604/95 |
| 5,556,370 | 9/1996 | Maynard | 600/142 |
| 5,562,726 | 10/1996 | Chuter | 623/1 |
| 5,619,177 | 4/1997 | Johnson et al. | 337/140 |
| 5,624,380 | 4/1997 | Takayama et al. | 600/146 |
| 5,662,621 | 9/1997 | Lafontaine | 604/281 |

DISTRIBUTED ACTIVATOR FOR A TWO-DIMENSIONAL SHAPE MEMORY ALLOY

BACKGROUND

The field of the present invention relates, in general, to Shape Memory Alloy (SMA) actuators and elements comprising these alloys. More specifically, the field of the invention relates to a spatially distributed activation means for controllably altering the local shape and deflection forces of a SMA sheet.

Materials which change their shape in response to external physical parameters are known and appreciated in many areas of technology. The geometry of a piezoelectric crystal, for example, is altered by an electric field. Similarly, the macroscopic shape of a SMA is sensitive to temperature. A SMA material undergoes a micro-structural transformation from a martensitic phase at a low temperature to an austenitic phase at a high temperature. When in the martensitic or low temperature phase, a SMA exhibits low stiffness and may be readily deformed up to 8% total strain in any direction without adversely affecting its memory properties. Upon being heated to its activation temperature, the SMA becomes two to three times stiffer as it approaches its austenitic state. In addition, at the higher temperature, the SMA attempts to reorganize itself on the atomic level to accommodate a previously imprinted or "memorized" shape. Useful motions and forces may be extracted from a SMA element as it attempts to move to its previously memorized shape. If permitted to cool, the SMA returns to its soft martensitic state.

A shape may be "trained" into a SMA by heating it well beyond its activation temperature to its annealing temperature and holding it there for a period of time. For a TiNi SMA system, the annealing program consists of geometrically constraining the specimen, and heating it to approximately 510 C for fifteen minutes. In most cases, functionality is enhanced by leaving in a certain amount of cold working by abbreviating the anneal cycle.

The point at which a SMA becomes activated is an intrinsic property of the material and is dependent on stochiometric composition. For a typical shape memory alloy such as TiNi (49:51), a change in alloy ratios of 1% produces a 200 C shift in transition temperature. Binary SMAs such as TiNi (sometimes referred to as Nitinol) can have a large range of transition temperatures. For Nitinol, atomic composition can be adjusted for a phase transition as high as 100 C and as low as −20 C or more. Sub-zero transition materials exhibit superelastic behavior. That is, they can reversibly endure very large strains at room temperature. In the medical community, superelastic formulations of Nitinol are commonly employed in "steerable" guidewires.

In contrast to the passive characteristics of a superelastic SMA, an actuator that must perform work on its environment requires a SMA capable of producing useful forces and motions for a given input of thermal energy. Because most thermal devices must expel their waste heat to the ambient environment, which in most cases is near room temperature, higher transition point SMAs are most commonly used as active actuator elements. During phase changes, a SMA will exhibit a maximum recoverable strain of up to 8% while producing a recovery force of 35 tons per square inch or more.

It is known to use SMA actuators in conventionally steerable elements such as catheters. One such application, as described in U.S. Pat. No. 4,543,090, involves a conventional steerable and aimable catheter using SMAs as the control elements. This device and other conventional steerable devices using SMA elements are severely limited in dexterity. Movement is limited to a single plane.

Upon cooling, a SMA element does not necessarily return to its pre-activation shape. Thus, to attain reversible motion, a means must be provided to return the inactive SMA element to a shape other than its trained shape. This can be accomplished with active or passive components. In the passive configuration, a return spring is provided such that it is just strong enough to fully deflect the SMA element in its martensitic state. When activated, the SMA element possesses enough force to overcome the return spring and perform work on the environment as it approaches its memorized state.

In an active or antagonistic configuration, each SMA element must be coupled to at least one other SMA element. When one SMA element has been heated to an activation threshold, it provides sufficient force to deflect the inactive actuator in a desired direction. Reverse motion is accomplished by reversing the order of activation.

A contraction-extension mechanism using joints made of an SMA material is shown by Komatsu et al. in U.S. Pat. No. 5,335,498. The described mechanism is an actuator strip with multiple joints. Joule heating elements or shape-controlling heaters are integrally attached to the component joints of the actuator. Passing sufficient current through the heaters causes the strip to contract at the joints in a bellows-like fashion. Three-dimensional motion can be imparted to objects by a geometrically suitable arrangement of such actuators. Unfortunately, the extension-contraction mechanism is also limited. Each strip contracts and extends in one direction only. Conventional arrangements of SMA strips to impart three-dimensional motion to objects are impractical because such structures are unduly large and cumbersome. This is due to the fact that such structures are not locally controllable and require excessive amounts of energy for their operation.

U.S. Pat. No. 5,405,337 issued to the present applicant teaches a flexible VLSI film containing SMA actuator elements and associated control and driver circuitry. The film is wrapped around any bendable element, such as a flexible, hollow tube, catheter, or the like. Thus, the SMA actuator elements are spatially distributed about the circumference of a bendable element. In one aspect of the invention, a distributed SMA array is provided on a flexible insulating film by sputtering a SMA alloy and patterning the individual islands of material with reactive ion etching (REI), plasma assisted etching, liftoff, or the like. The individual SMA actuators can then be directly heated with electrical current (conductive SMA), or may be heated by contact with an adjacent heat source (non-conductive SMA). Since the SMA actuator film is wrapped around a flexible tube, activation of the SMA film achieves movement in three dimensions.

Although this approach is effective, the associated manufacturing costs are high. Patterning the SMA film using conventional VLSI methods can be expensive and sputtered SMA films thicker than approximately 10 microns are difficult to produce at the present time. The stress accumulated within a sputtered film greater than this thickness usually causes the film to rupture. However, current efforts involving heated substrate sputtering may mitigate these damaging internal stresses.

A second problem with sputtered SMA materials is that the atomic composition and form of the sputtered film may differ significantly from that of the parent target. For example, in the case of a binary SMA such as 50/50 TiNi, when the sputtering ions strike the surface of a target and liberate individual atoms of Ti and Ni, the difference in vapor pressure between these two elements produces a significant change in the 50/50 composition in the vapor phase and subsequent deposition phase. In addition, the grain structure of the deposited film must be carefully controlled for efficient SMA actuation.

What is needed then, is a low cost method for producing a distributed SMA actuator array which does not rely heavily on VLSI patterning and sputtering techniques. In particular, it would be advantageous to obtain a sheet of SMA material directly from bulk, wire or plate stock without adversely altering grain structure or composition. A distributed array of addressable heaters and associated electronics could then be patterned directly on the SMA film. It would also be beneficial to limit the number of cuts made in the SMA film such that an automated saw, abrasive water jet, laser cutter, electronic discharge machining, or the like, could be employed to an economic advantage.

SUMMARY

It has been found that SMA elements can be made more efficiently and with low cost by using a two-dimensional sheet comprising a SMA material with a distributed activation means for heating the SMA material, mounted on the sheet. The two-dimensional sheet has a sufficiently small thickness to limit the lateral flow of the heat. Depending on the type of SMA material, the SMA elements can be electrically conductive or electrically insulating. The distributed activation means comprises at least one heating element disposed on the two-dimensional SMA sheet and disbursed on an adjacent portion of the two-dimensional sheet for locally heating this portion. In response to an applied activation energy, the activated portion of the two-dimensional sheet assumes a predetermined shape.

In the case of electrically conducting SMA materials an electrical insulator is positioned between the two-dimensional sheet and the heating elements. The electrical insulator is sufficiently thin to ensure that the heat generated by the heaters is transferred to the SMA residing in the two-dimensional Sheet. Preferably, the electrical insulator is selected from the group consisting of insulating organic polymers, inorganic insulators, silicon oxide, silicon nitride, silicon dioxide, silicon carbide, or the like, an polytetrafluoroethylene. For SMA materials which are themselves electrical insulators no additional electrical insulator is required.

A control unit is provided for passing an electrical current through a combination of the heating elements. In this manner each of the heating elements belonging to the combination heats its adjacent portion of the two-dimensional sheet and causes this portion to assume a predetermined shape. As a result, the two dimensional sheet assumes a predetermined shape.

The SMA sheet can be pre-trained to assume a specific shape, either prior to patterning of the heaters or after the heaters have been defined.

Preferably, the heating elements and the electrical insulation are fabricated according to VLSI or micro-machining techniques which are well known to those skilled in the art. The control mechanism preferably includes a current generator and a control unit for selecting a desired combination of heating elements. Additionally, one or more deflection sensors such as strain gages are mounted on the two-dimensional sheet to indicate the local deflection state. These sensors can be used to convey information representative of the resultant shape of the two-dimensional sheet.

An aspect of the invention provides for depositing additional protective layers on the two-dimensional sheet. Such protective layers can be used for mechanical stabilization or for a controlled degree of thermal isolation. Another aspect of the invention increases thermal transfer performance by including an array of Peltier elements cooling fans, or the like.

In another aspect of the invention known methods of open and closed loop control are enhanced by the inclusion of one or more thermal sensors mounted on the SMA sheet. Thermal sensors advantageously achieve rapid cycling of the SMA actuators without exceeding a maximum operating temperature.

An aspect of the invention also comprises a method for selectively activating the two-dimensional sheet containing the SMA. This method is applicable to electrically conducting and electrically insulating SMA materials. In one aspect, the SMA is pre-trained to assume a predetermined shape before completion of the two-dimensional sheet. Alternatively, the SMA can be pre-trained after the heater array has been fabricated.

Finally, a two-dimensional SMA sheet can be jointed to create a three-dimensional structure. The resulting structure is capable of unlimited motion in three dimensions. By affixing two or more SMA activator sheets to a flexible substrate one is also able to provide planar or full three dimensional motion. The particulars of the invention are elucidated in the below description with reference to the attached drawing of figures.

DESCRIPTION

Figure 1:
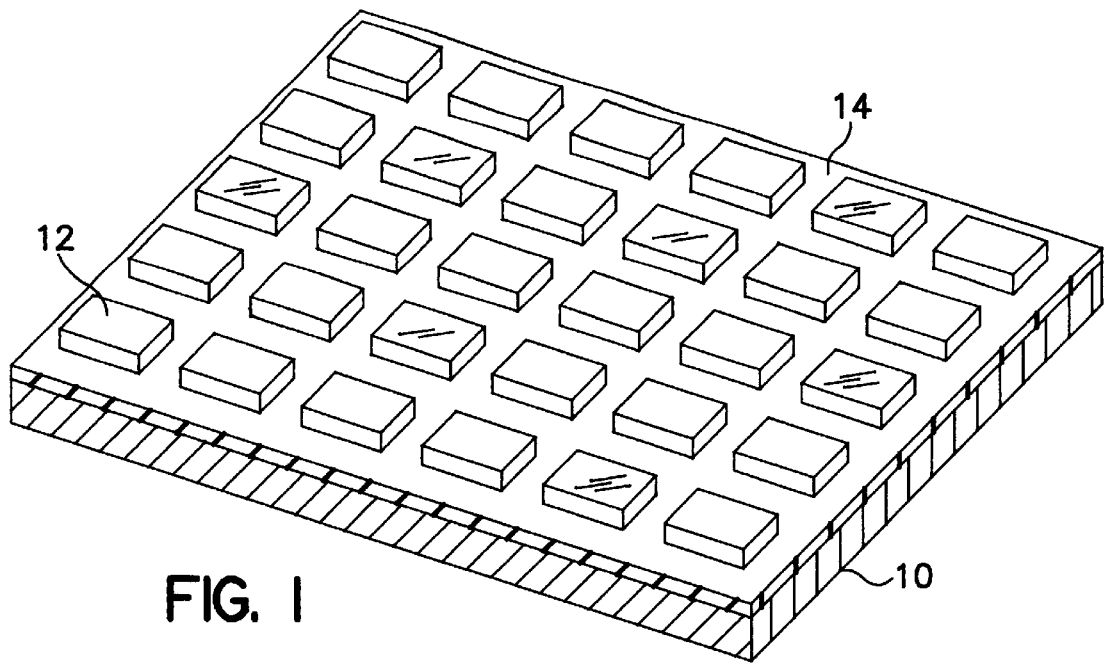
FIG. 1 is an isometric view of a deactivated two-dimensional sheet according to the invention.

A simplified embodiment of a two-dimensional sheet 10 according to an aspect of the invention is shown in FIG. 1. The basic concepts discussed here can be applied directly to practical embodiments which will be described later. In this case sheet 10 is made entirely of a Shape Memory Alloy (SMA) chosen from the group of electrically conductive materials. Most common examples include TiNi alloys and CuZnAl alloys. Other alloys can also be used. The ratio of the thickness of sheet 10 to the lateral extent of heating element 12 should be preferably as small as possible, while still capable of maintaining the integrity of sheet 10.

SMA sheet 10 is produced by a variety of common machining methods; such as rolling of thin foils from were or thin plate stock, sectioning thin wafers from bar stock, or like methods. At present, sectioning of thin wafers from bar stock is preferred. Wafers of SMA material may be sliced from bar stock using a conventional band saw, a cold saw, an annular diamond wet saw, or electro-discharge machining (EDM) or like methods. The resulting wafer can be heat treated to a flat condition and precision-ground to any desired thickness. SMA bulk properties are assured as the material is obtained directly from bulk. The SMA material contained in sheet 10 can be pre-trained prior to assembly or left untrained. The choice depends on the eventual application.

A plurality of heating elements 12 are positioned on top of SMA sheet 10 and insulated from sheet 10 by an electrically insulating layer 14. It is most convenient to laminate or otherwise deposit electrically insulating layer 14 on sheet 10. Electrically insulating layer 14 prevents current leakage between heating elements 12 and electrically conducting sheet 10. Electrically insulating layer 14 also preferably is a good thermal conductor. Preferred insulating materials include polyimide or silicon nitride $Si_xN_y$. The thickness of electrically insulating layer 14 should be small in relation to its lateral extent. For example, electrically insulating layer 14 may be a 2000 Å silicon nitride layer to ensure adequate thermal coupling, and to ensure thermal conductivity between heating elements 12 and sheet 10.

In the simplified embodiment of FIG. 1, heating elements 12 are in the form of thin film resistors. Most preferably, heating elements 12 are ohmic heaters or other similar devices capable of converting electrical current to thermal energy. They can comprise any conventional resistive material such as TiW or TaO. Conveniently, the resistive material is first deposited and patterned on layer 14 by well known VLSI or micro-machining techniques. Then, heating elements 12 are patterned or otherwise formed according to well-known techniques.

Figure 3:
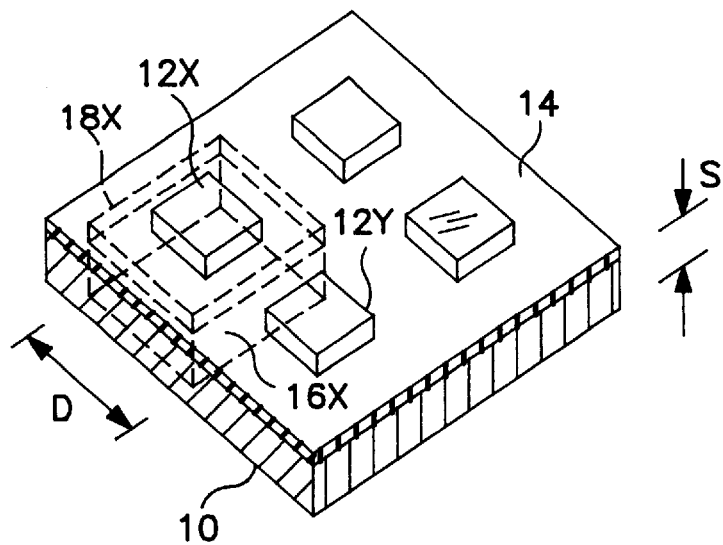
FIG. 3 is an isometric view of a portion of the two-dimensional sheet of FIG. 1.

In FIG. 3 the thickness of sheet SMA 10 is labeled by S. For clarity, a particular heating element 12X has been selected to explain the details of the invention. Heating element 12X has associated with it an adjacent portion 16X of SMA sheet 10. As shown, heating element 12X has associated with it a section 18X of electrically insulating layer 14 as well. Portion 16X is located directly underneath heating element 12X. The width of portion 16X is denoted by D. As shown, heating element 12X provides heat to portion 16X exclusively. Heat propagates through section 18X and into section 16X which represents a localized portion of SMA sheet 10.

Figure 2:
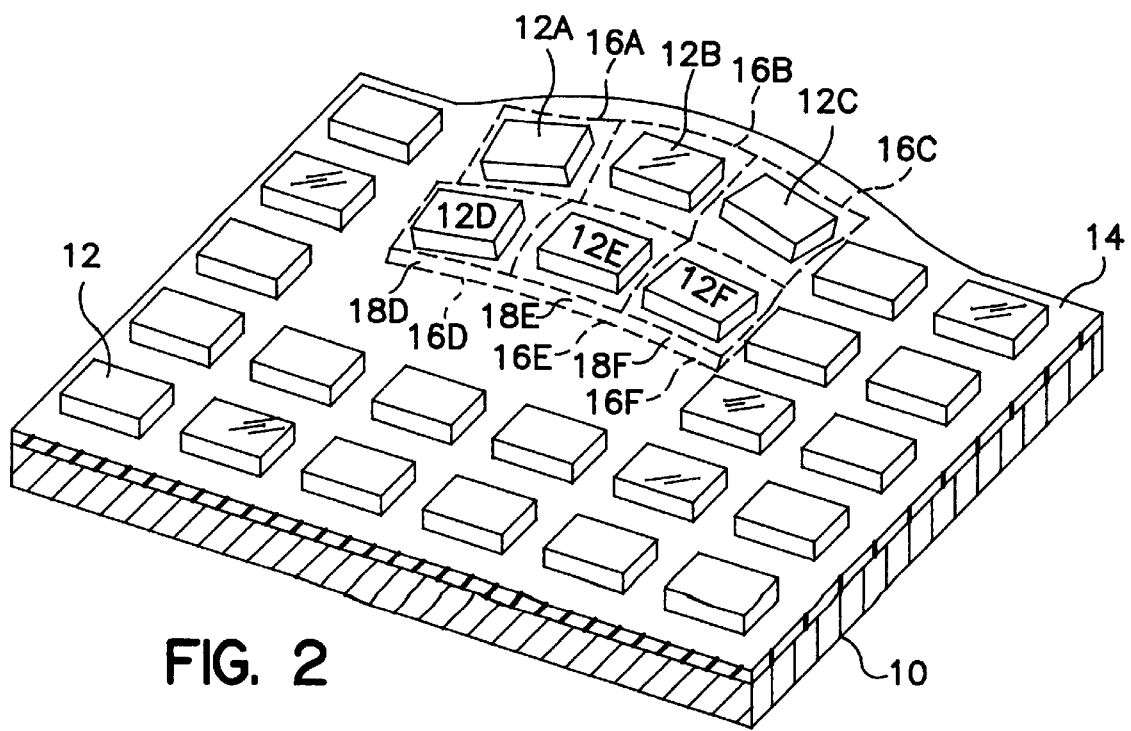
FIG. 2 is an isometric view of the two-dimensional sheet of FIG. 1 in the activated state.

The operation of the simplified embodiment is best understood by comparing FIG. 1 and FIG. 2. In this case, the SMA material has been pre-trained to assume a predetermined shape when thermally activated to an activation threshold temperature. In FIG. 1, SMA sheet 10 is shown in an inactive state.

FIG. 2 shows a particular case wherein six heating elements 12, labeled as 12A–12F, are providing heat. Consequently, the heat traverses section 18A–18F of insulating layer 14 and causes adjacent portions 16A–16F of SMA sheet 10 to reach activation threshold. As a result, portions of 16A–16F assume a well-defined shape and in the process, provide useful activation forces. As shown, the local deformation is upward convex. Once portions 16A–16F assume their shape, the areas of sheet 10 surrounding those portions deform in accordance with a predetermined memory characteristic. In fact, entire sheet 10 assumes a resultant shape due to local changes as dictated by its geometry. In the simple case of FIG. 2, the remainder of sheet 10 remains flat or otherwise returns to its neutral shape; neutral meaning its inactive state. More complex resultant shapes will be described in later embodiments.

Figure 4A:
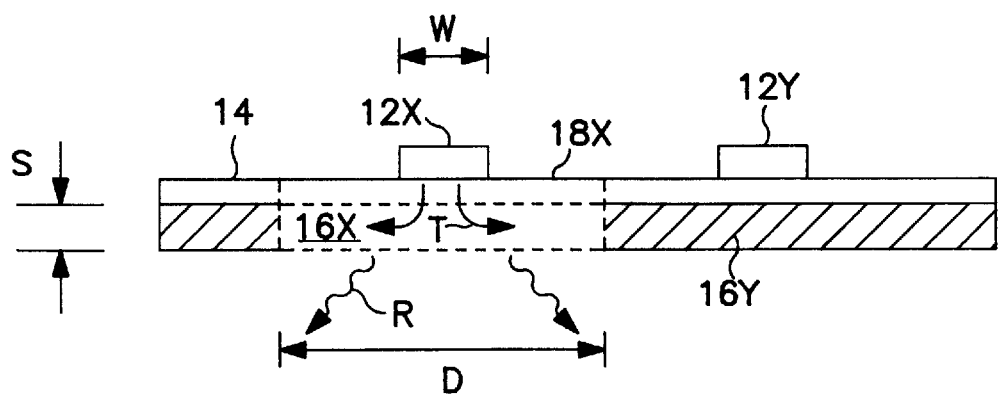
FIG. 4A is a cross section of the portion of the two-dimensional of FIG. 4A.

The principles behind the heating process and the shape assumed by adjacent portions 16 are best illustrated in FIG. 4A. We consider one heating element 12X. For clarity, the predetermined shape assumed by adjacent portion 16X upon heating has not been shown. The heat generated by element 12X, whose width is indicated by W, passes along arrows through insulating layer 14. In particular, the thermal energy traverses section 18X of layer 14. Layer 14 is proportionally very thin compared to the lateral dimensions, and thus section 18X readily transfers the heat to sheet 10. Once in sheet 10 the heat propagates throughout adjacent portion 16X.

Figure 4B:
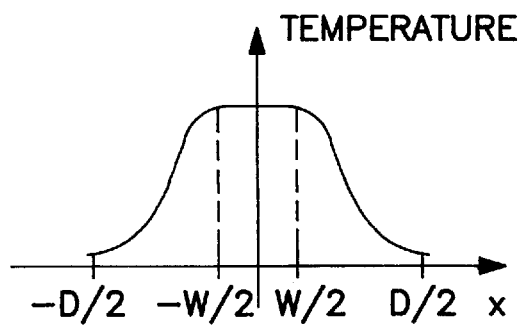
FIG. 4B is a graph of the temperature distribution in the portion of FIG. 4A.

Graph 4B represents temperature distributions at an arbitrary fixed depth below heater 12X. The graph in FIG. 4B shows the temperature distribution laterally, in the X direction, inside portion 16X. Directly under element 12X the temperature remains at a maximum, as indicated by the flat portion of the curve from –W/2 to +W/2. In other words, the heat delivered to portion 16X does not propagate to other portions 16, e.g., portion 16Y. Instead, the heat radiates along arrows R out of sheet 10 before reaching other portions 16.

Figure 5:
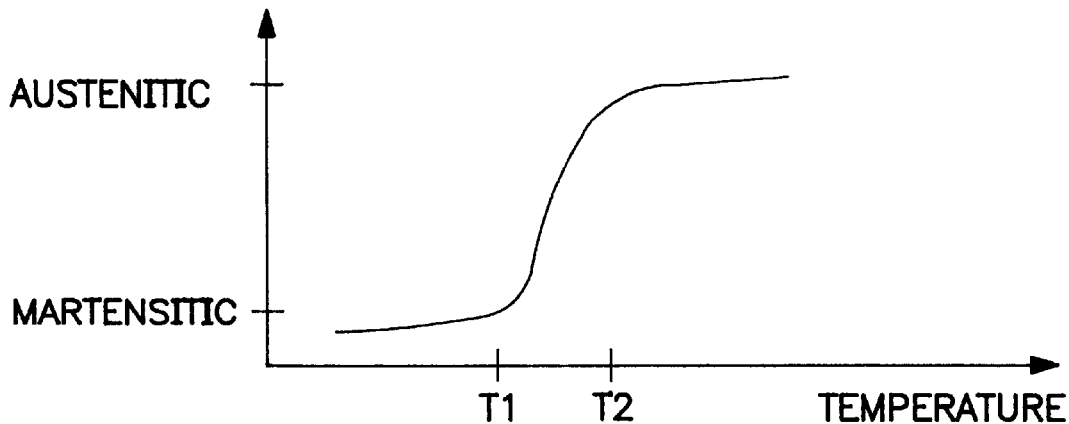
FIG. 5 is a graph of the transition between the martensitic and austenitic states as a function of temperature.

As already mentioned, the shape of adjacent portions 16 depends on the pre-trained shape of the SMA or sheet 10 in those regions. Also, the shape depends on the temperature maintained in portions 16. Full conformity to the pre-trained shape is achieved when the temperature in portions 16 is equal or higher than the critical temperature at which the SMA material attains the austenitic state. This is best shown in the graph of FIG. 5. At temperatures below $T_1$ the SMA material remains pliable, as dictated by the martensitic properties. Therefore, portions 16 maintained at or below $T_1$ will conform to the shape imparted to them by the surroundings. The transition to the austenitic state occurs between temperatures $T_1$ and $T_2$. When portions 16 are kept in this temperature range they will assume an intermediate shape between the relaxed and pre-trained forms. Careful thermal regulation thus allows one to vary the shape of any portions 16 of sheet 10 in a continuous manner.

The overall structure of sheet 10 where heating elements 12 are mounted directly on sheet 10 with only layer 14 interposed between them is very simple. The assembly process is straightforward and low-cost.

Figure 6:
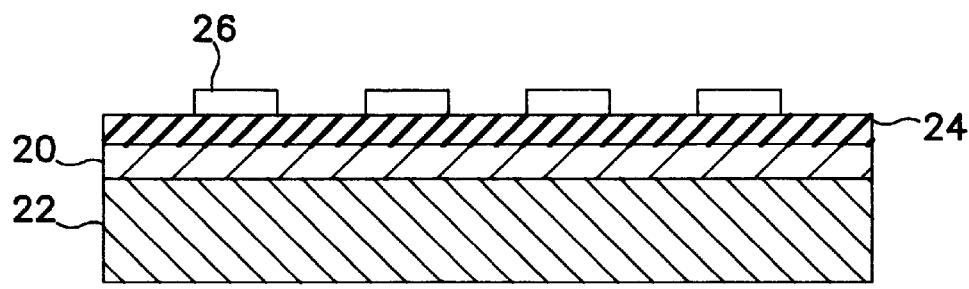
FIG. 6 is a cross section of a two-dimensional sheet with an insulating layer and a coating layer.

Another embodiment of the invention is shown in FIG. 6. Here a two-dimensional sheet 20 of SMA material is placed on a coating layer 22. In this case, layer 22 is sufficiently thick to provide mechanical stability.

A thin insulating layer 24 is disposed on top of sheet 20 to provide electrical insulation between heating elements 26 and sheet 20. Layer 24 is thin enough and has appropriate thermal properties to permit the free flow of heat from elements 26 to sheet 20. In this embodiment the SMA material of sheet 20 is also electrically conducting (e.g., TiNi alloy or CuZnAl alloy).

The operation of this embodiment is analogous to the operation of the first one. The added stability of coating layer 22 ensures conformity to a well-defined shape when all portions of sheet 20 are in the martensitic state.

Figure 7:
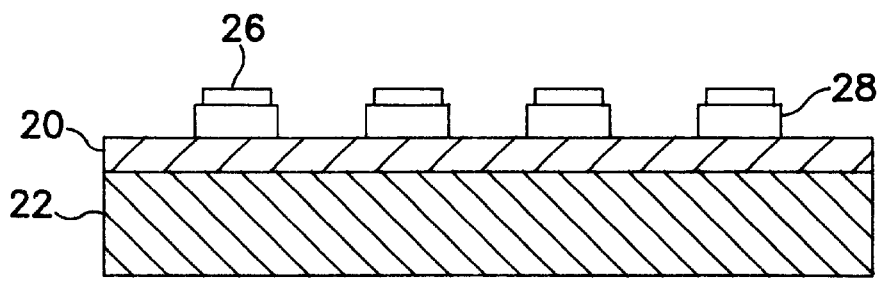
FIG. 7 is a cross section of a two-dimensional sheet with point-wise applied insulating layer and a coating layer.

The embodiment of FIG. 7 exhibits sheet 20 of electrically conducting SMA with a coating layer 30 acting as substrate. In this case layer 30 is chosen from materials which are chemically inert and stable to protect sheet 20 from adverse effects.

Electrical insulation between heating elements 26 and sheet 20 is provided by sections of electrical insulation sections 28 deposited point-wise under elements 26. Such structure can be produced by initially applying a layer of insulating material and a layer of heating material. Then, elements 26 and a corresponding electrical insulation sections 28 are fashioned by etching or another well-known process. Preferably, a well known VLSI technique or a micro-machining technique is employed for this purpose.

Figure 8:
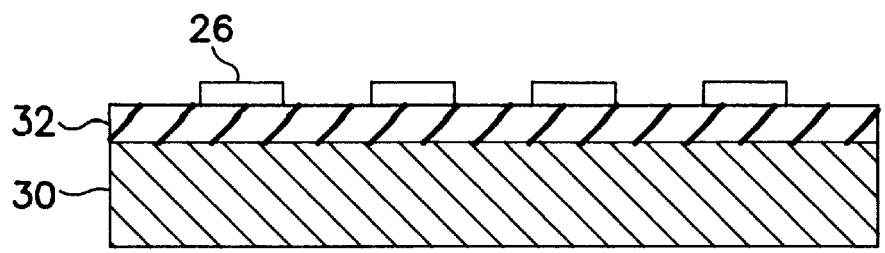
FIG. 8 is a cross section of a two-dimensional sheet with a coating layer.

FIG. 8 shows yet another embodiment in which a two-dimensional sheet 32 is made up of an electrically insulating SMA material. In this configuration no insulation is necessary. Consequently, heating elements 26 are mounted directly on sheet 32. A coating layer 30 functioning as substrate is once again provided to afford mechanical stability and resistance. It is preferable that layer 30 also be a good thermal conductor to aid in the dissipation of heat from sheet 32.

The embodiments of FIGS. 6–8 all operate in the manner set forth above. The modifications introduced are intended to aid one skilled in the art in selecting the appropriate structure given a set of technical requirements.

PREFERRED EMBODIMENT

Figure 9:
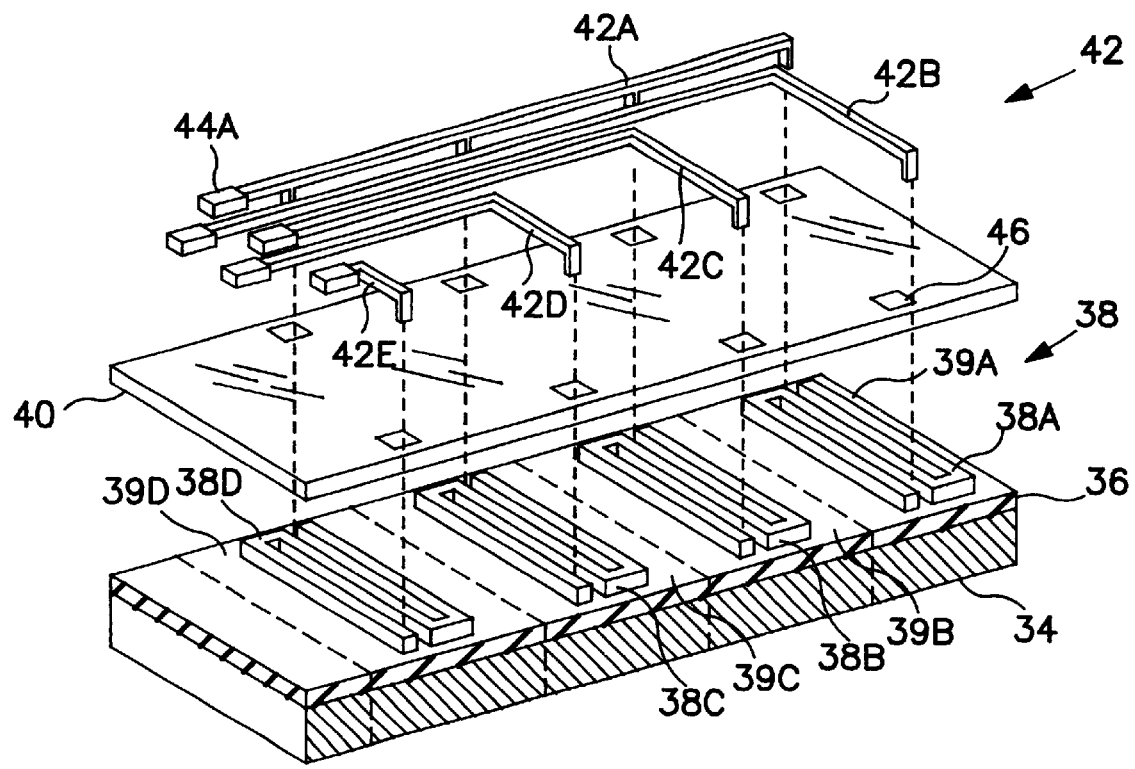
FIG. 9 is an exploded view illustrating the assembly of a two-dimensional sheet and the activation elements according to the invention.

The preferred embodiment is shown in FIG. 9. A two-dimensional sheet 34 of an electrically conducting Shape Memory Alloy (SMA) material, preferably a NiTi alloy is coated with insulating layer 36. Preferably, layer 36 is made of $Si_xN_y$ or polyimide and is sufficiently thin to readily conduct heat.

Patterned heating elements 38 are located on layer 36. Elements 38 are obtained by first sputtering TiW or TaO on top of layer 36 and then performing a patterning step. Heating elements 38 offer a very high resistance. In the preferred embodiment elements 38A–38D have a zig-zag shape. This enables them to ensure better heat distribution in sheet 34 when active.

A second insulating layer 40 is provided on top of elements 38 and layer 36. Preferably, layer 40 is made of a flexible electrical insulation such as polyimide, which can be spun coated onto elements 38 and layer 36. A number of through-holes 46 are opened in layer 40 to permit electrical contact with elements 38. Holes 46 are sensibly aligned with the terminal portions of elements 38.

A set of conduction lines 42 are patterned on top of layer 40. Preferably, conduction lines 42 are made of a flexible and highly conductive material such as gold. Lines 42 can be defined by patterning or other suitable techniques. A common return line 42A is laid out to provide electrical contact with the left terminals of all elements 38. Return line 42A saves surface area of top of layer 40 and is desirable as long as all elements 38 are not addressed simultaneously on a continuous basis. If continuous activation is required, then an additional full width layer would be dedicated for the return path. The other lines, 42B–42E are in electrical contact with the right terminals of elements 38 respectively.

External electrical connections are made to contact pads 44A–44E, corresponding to lines 42A–42E. For this purpose, pads 44A–44E are designed much thicker than lines 42A–42E. The actual electric connections are made with wire bonding or similar means.

Once the entire structure on sheet 34 is assembled, the SMA is "trained" by forcing sheet 34 to assume a resultant shape using well-known methods. For example, sheet 34 is formed on a mandrel and fixed in place with a clamp. The entire fixture is then placed in an annealing furnace, preferably purged with an inert gas, at approximately 450 C for about 30 minutes. Upon cooling the film is released from the mandrel. At this time sheet 34 is operationally ready.

Figure 10:
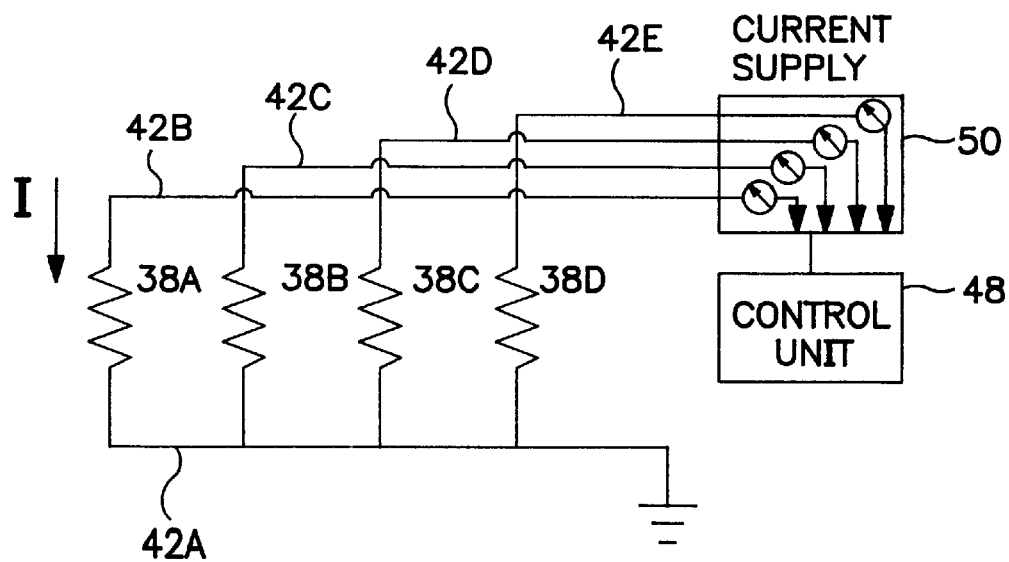
FIG. 10 is a diagram showing the equivalent circuit of the activation mechanism.

The electrical diagram showing the electrical connections of the preferred embodiment is found in FIG. 10. A control unit 48 is connected to a current supply 50. Preferably, both unit 48 and supply 50 are located away from sheet 34. Unit 48 is preferably a micro-processor capable of selecting a desired combination of elements 38. Current supply 50 is preferably an adjustable source capable of delivering current to the selected combination of elements 38. Lines 42A–42E are connected directly to supply 50. Elements 38A–38D are shown as resistors. Return line 42A is grounded.

During operation control unit 48 selects a combination of elements 38 to be activated. It then sends a corresponding command to supply 50. Supply 50 responds by delivering current to elements 38 of the chosen combination. For example, elements 38A and 38D are chosen. Current is delivered to elements 38A and 38D and the corresponding adjacent portions 39A and 39D assume a well-defined shape. If the current is sufficiently large and the temperature maintained in adjacent portions 39A and 39D is above $T_2$ (see FIG. 5) then portions 39A and 39D will assume their pre-trained shape. If the temperature is between $T_1$ and $T_2$ portions 39A and 39D will assume an intermediate shape. Because supply 50 is adjustable the proper current can be selected during operation and adjusted on an empirical basis. Consequently, the shape of portions 39A and 39D can be varied as necessary.

Figure 11:
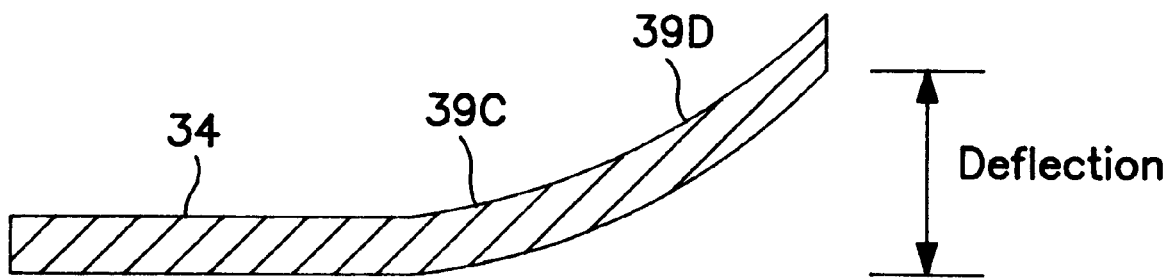
FIG. 11 is a side view illustrating the deflection of a two-dimensional sheet according to the invention.
Figure 12:
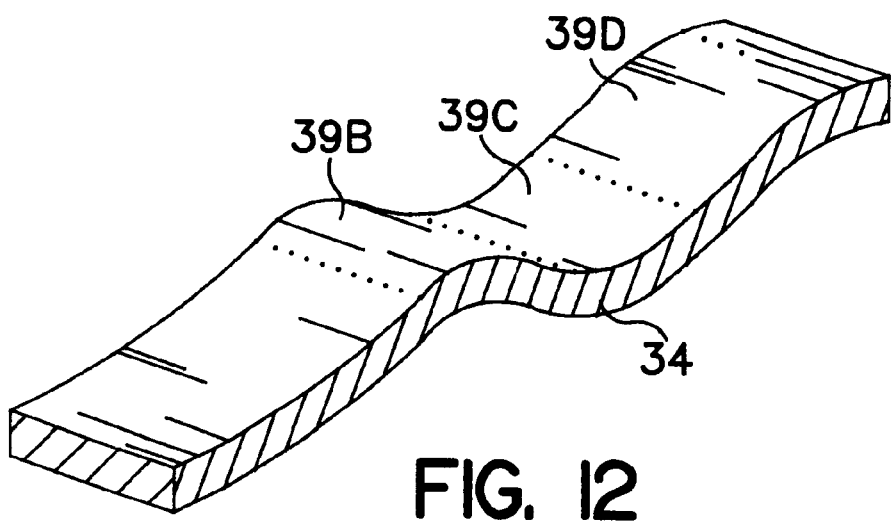
FIG. 12 is a perspective view illustrating a complex pre-trained shape of a sheet according to an aspect of the invention.

FIG. 11 illustrates the resultant shape of sheet 34 when adjacent portions 39C and 39D are selected. It is assumed that the SMA was pre-trained to curve upward along its entire length. Thus, together, deflections in portions 39C and 39D contribute to a much larger total deflection. FIG. 12 illustrates another possible resultant shape of layer 34 when sections 39B–39D are heated and the SMA was pre-trained to assume an S-shape. Throughout the description it is understood that the SMA of sheet 34 can be trained before or after assembly. Training before assembly can be preferable when working with materials which would be damaged if trained together with the SMA, e.g., due to the high annealing temperatures.

Figure 14:
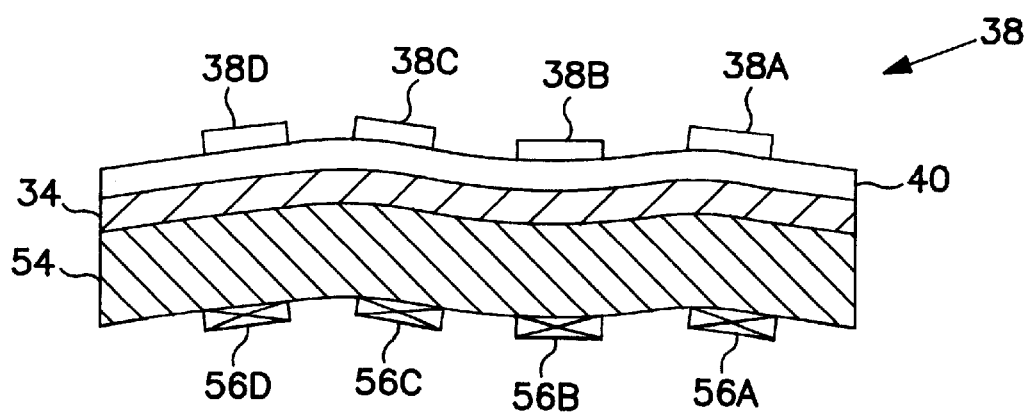
FIG. 14 is a cross sectional view of a two-dimensional sheet with deflection sensors.

In another embodiment similar to the preferred embodiment sheet 34 has a coating layer 54 as shown in FIG. 14. For better understanding, the deflections in sheet 34 have been indicated. Deflection sensors 56A–56D are positioned on layer 54. Sensors 54A–54D can be either angular deflections sensors, extension deflection sensors such as a strain gage, or bend sensors. A bend sensor is a strain gage disposed for measuring bending strain and thus angular deflection. All of these devices are well known in the art. In this case sensors 56A–56D have been placed in locations corresponding to those of elements 38. Depending on the geometry and application different placement may be preferable.

Figure 13:
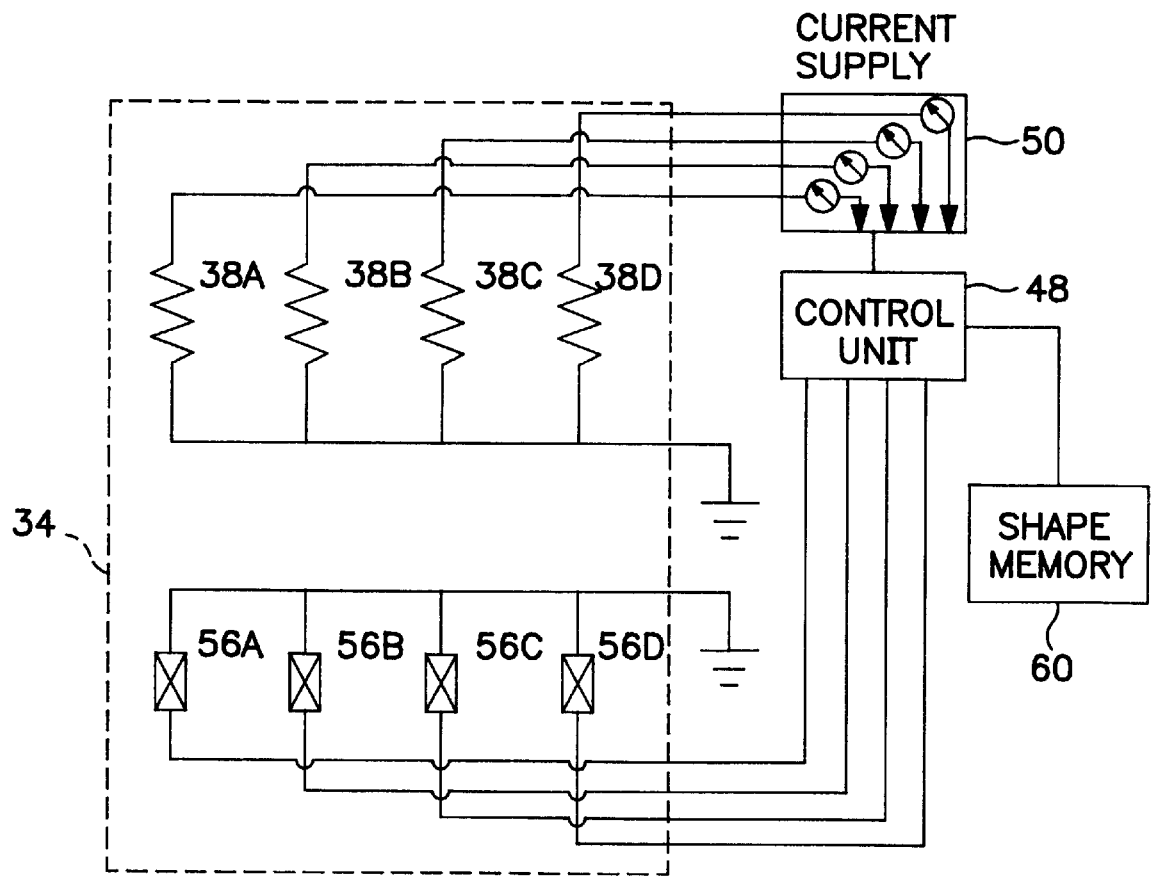
FIG. 13 is a diagram showing the equivalent circuit of an embodiment using deflection sensors.

The electrical diagram with sensors 56 is shown in FIG. 13. The dotted line represents elements mounted on sheet 34. While the connections to elements 38A–38D remain the same, all sensors 56A–56D are wired to control unit 48 via lines 58A–58D respectively. In this manner unit 48 can receive signals representative of the local deflection from each one of sensors 56A–56D individually. A shape memory 60 is connected to unit 48. Memory is capable of mapping the resultant shape of sheet 34 based on information delivered from sensors 56.

Preferably, memory 60 has an inventory of resultant shapes produced by known combinations of elements 38. In other words, memory 60 is capable of recalling mapped resultant shapes positions and storing new ones. In the most preferred embodiment memory 60 can also store the actual current values corresponding to intermediate shapes of adjacent portions. This means that in operation shapes can be recalled and stored at will. The embodiment is thus highly versatile and practical for any diverse applications, e.g., guiding catheters.

Figure 15:
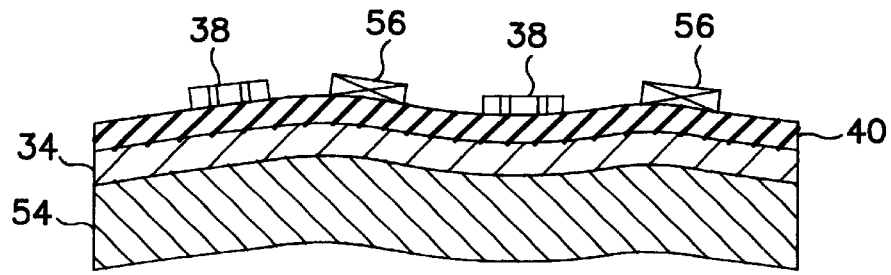
FIG. 15 is a cross sectional view of a two-dimensional sheet with deflection sensors mounted next to heating elements.
Figure 16:
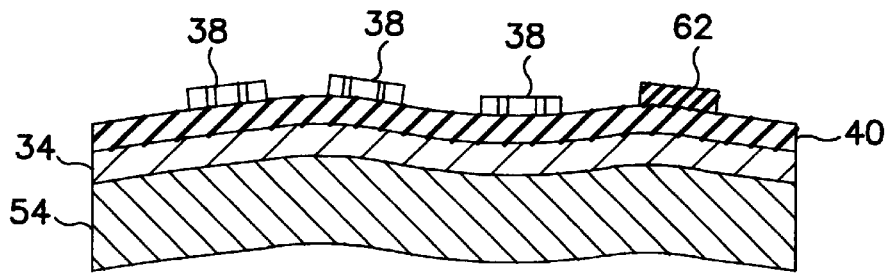
FIG. 16 is a cross sectional view showing a two-dimensional sheet with a temperature sensor.

FIG. 15 shows yet another embodiment which differs from the above only in that sensors 56 are positioned between elements 38. FIG. 16 shows another modification in which a temperature sensor 62 is mounted between elements 38. This is advantageous for monitoring the temperature of sheet 34. In a particularly preferred embodiment this data is stored in memory 60. Checking the temperature form sensor 62 during operation can prevent overheating and other related malfunctions. Of course, more than one thermal sensor 62 can be provided. Ideally, a number of such sensors 62 can be provided. Ideally, a number of such sensors 62 are optimally positioned on sheet 34.

Figure 17:
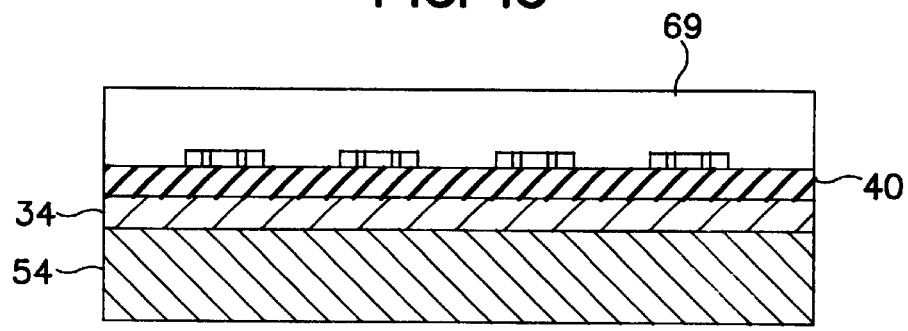
FIG. 17 is a cross sectional view of a two-dimensional sheet with protective coating applied over the eating elements.

FIG. 17 shows the embodiment of FIG. 14 in the martensitic state encapsulated in a top coating layer 64. Layer 64 is applied to protect the electrical connections and elements 38 in particular from damaging environmental factors, e.g., corrosive environments.

Figure 18:
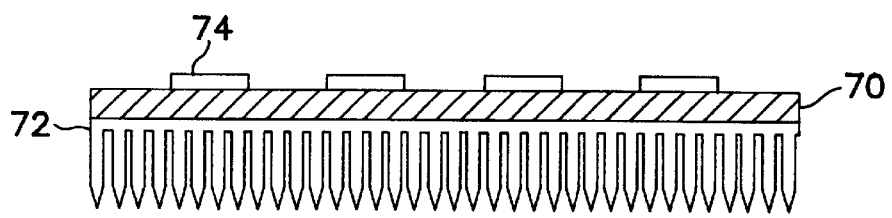
FIG. 18 is a cross section of a two-dimensional sheet using vanes for heat dissipation.
Figure 19:
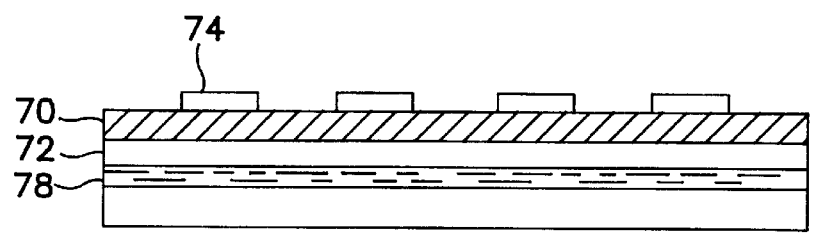
FIG. 19 is a cross section of a two-dimensional sheet using water ducts for heat dissipation.

FIG. 18 and FIG. 19 show two ways in which a two-dimensional sheet 70 of SMA can be cooled. For simplicity, all other elements, except for heating elements 74, have been omitted. In FIG. 18 the cooling element is a set of fins 72 in direct contact with sheet 70. This arrangement ensures efficient heat transfer and dissipation. Similarly, the structure id FIG. 19 efficiently dissipates heat using a substrate layer 76 with ducts 78 (only one shown). Ducts 78 carry a coolant, e.g., water, which absorbs and carries away the waste thermal energy.

While the invention has been described in connection with what is presently considered to be the most practical and preferred embodiments, it is to be understood that the invention is not limited to the disclosed embodiments, but on the contrary, is intended to cover various modifications and equivalent arrangements included within the spirit and scope of the appended claims. For example, a Peltier device could also provide an equivalent solution to heat dissipation. Therefore, persons of ordinary skill in this field are to understand that all such equivalent structures are to be included within the scope of the following claims.

What is claimed is:

1. A distributed activation system, comprising a unitary two-dimensional continuous sheet of shape memory alloy having a sufficiently small thickness to limit the lateral flow of heat;

an insulator positioned on a surface of said sheet of shape memory alloy; and a plurality of independently controllable heating elements patterned on said insulator, each one of an independently controllable heating element of said plurality providing local heating of an adjacent portion of said sheet such that said adjacent portion assumes a predetermined shape when activated to its threshold temperature, said plurality of independently controllable heating elements being configured to be coupled to a heater control device that selectively passes an electrical current through at least one heating element to provide local heating of said sheet.

2. The distributed activation system of claim 1 further comprising a plurality of deflection sensors mounted on said sheet to indicate the local deflection state of said sheet.

3. The distributed activation system of claim 2 wherein said heater control device is configured to be coupled to said deflection sensors, such that the local deflection state of said sheet is communicated to said heater control device.

4. The distributed activation system of claim 3 wherein said heater control device further comprises a shape memory means for position mapping of the sheet.

5. The distributed activation system of claim 4 wherein said deflection sensors are selected from the group consisting of angular deflection sensors, extension deflection sensors, and bend sensors.

6. The distributed activation system of claim 1 further comprising thermal sensors mounted on said sheet for measuring the temperature of said sheet.

7. The distributed activation system of claim 1 wherein said sheet is trained prior to fabrication.

8. The distributed activation system of claim 1 wherein said sheet is made of a material selected from the group consisting of TiNi alloys and CuZnAl alloys.

9. This distributed activation system of claim 1 further comprising a substrate layer deposited on said sheet to dissipate the heat deposited in said adjacent portions.

10. The distributed activation system of claim 7 wherein said predetermined shape assumed by said adjacent portion is a pre-trained shape.

11. The distributed activation system of claim 7 wherein said predetermined shape assumed by said adjacent portion is an intermediate shape.

12. The distributed activation system of claim 9 wherein said substrate layer further comprises cooling elements selected from the group consisting of Peltier elements, cooling fins, and water channels.

13. A distributed activation system, comprising:
- a two-dimensional sheet of an electrically insulative shape memory alloy having a sufficiently small thickness to limit lateral flow of heat;
- a plurality of independently controllable heating elements positioned on a surface of said two-dimensional sheet, each one of an independently controllable heating element of said plurality providing local heating of an adjacent portion of said sheet for locally heating said adjacent portion such that said adjacent portion assumes a predetermined shape; and
- control means for passing an adjustable electrical current through at least one of said heating element of said plurality of independently controllable heating elements, such that said heating element of the plurality heats said adjacent portion and said adjacent portion assumes said predetermined shape so that said two-dimensional sheet assumes a resultant shape.

14. The distributed activation means of claim 13 wherein said two-dimensional sheet of shape memory alloy is pre-trained with a final shape.

15. The distributed activation means of claim 13 wherein said predetermined shape assumed by said adjacent portion is the final pre-trained shape.

16. The distributed activation means of claim 13 wherein said predetermined shape assumed by said adjacent portion is an intermediate shape.

17. The distributed activation means of claim 13 wherein said two-dimensional sheet of shape memory alloy is not trained with a final shape.

18. The distributed activation means of claim 13 wherein said heating elements are fabricated by a technique chosen from the group consisting of VLSI and micro-machining.

19. The distributed activation means of claim 13 wherein said control means comprises a current generator and a control unit for selecting said combination of said heating elements.

20. The distributed activation means of claim 13 further comprising a plurality of deflection sensors mounted on said two-dimensional sheet to indicate the local deflection state of said two-dimensional sheet.

21. The distributed activation means of claim 13 further comprising a coating layer deposited on said two-dimensional sheet.

22. The distributed activation means of claim 13 further comprising a substrate layer deposited on said two-dimensional sheet to dissipate the heat deposited in said adjacent portions.

23. The distributed activation means of claim 13 further comprising thermal sensors mounted on said two-dimensional sheet for measuring the temperature of said two-dimensional sheet.

24. The distributed activation means of claim 20 wherein said control means is connected to said deflection sensors, such that the local deflection state of said two-dimensional sheet is communicated to said control means and said control means computes said resultant shape.

25. The distributed activation means of claim 20 wherein said deflection sensors are selected from the group consisting of angular deflection sensors, extension deflection sensors, and bend sensors.

26. The distributed activation means of claim 24 wherein said control means further comprises a shape memory means for position mapping and for storing said resultant shape and said combination of said heating elements.

27. The distributed activation means of claim 22 further comprising cooling means selected from the group consisting of Peltier elements, cooling fins, and water channels.

28. A method for selective activation of a two-dimensional sheet of electrically conductive shape memory alloy having a sufficiently small thickness to limit lateral flow of heat comprising the following steps:
- placing a plurality of heating elements on said two-dimensional sheet such that each one of a heating element of said plurality is assigned to an adjacent portion of said two-dimensional sheet for locally heating said adjacent portion such that said adjacent portion assumes a predetermined shape;
- electrically insulating said two-dimensional sheet from said plurality of heating elements;
- c) providing a thermally conductive path between said plurality of heating elements and adjacent portions of said two-dimensional sheet; and
- d) passing an electrical current through at least one of said heating element of said plurality to an adjacent portion to assume said predetermined shape so that said two-dimensional sheet assumes a resultant shape.

29. The method of claim 28 further comprising the step of pre-training said two-dimensional sheet to assume a pre-trained shape.

30. The method of claim 28 wherein said step of pre-training is conducted before assembly of said two-dimensional sheet.

31. The method of claim 28 wherein said step of pre-training is conducted after assembly of said two-dimensional sheet.

32. The method of claim 28 wherein the two-dimensional sheet is configured for attachment to at least an additional two-dimensional sheet of shape memory alloy.

* * * * *